(12) United States Patent
Rochetin et al.

(10) Patent No.: US 8,002,839 B2
(45) Date of Patent: Aug. 23, 2011

(54) SURGICAL APPARATUS FOR IMPLANTATION OF A PARTIAL OR TOTAL KNEE PROSTHESIS

(75) Inventors: Olivier Rochetin, Marcilly le Chatel (FR); Yves-Alain Ratron, Grenoble (FR); Alain Tornier, Saint Ismier (FR)

(73) Assignee: Tornier SAS, St. Ismier (FR)

( * ) Notice: Subject to any disclaimer, the term of this patent is extended or adjusted under 35 U.S.C. 154(b) by 1073 days.

(21) Appl. No.: 11/401,415

(22) Filed: Apr. 11, 2006

(65) Prior Publication Data
US 2007/0270718 A1 Nov. 22, 2007

(30) Foreign Application Priority Data
Apr. 13, 2005 (FR) ...................................... 05 03675

(51) Int. Cl.
*A61F 2/38* (2006.01)
*G06G 7/48* (2006.01)
(52) U.S. Cl. ...................................... 623/20.14; 703/11
(58) Field of Classification Search .................... 703/11; 623/20.14
See application file for complete search history.

(56) References Cited

U.S. PATENT DOCUMENTS

| 5,171,289 A | 12/1992 | Tornier |
| 5,314,485 A | 5/1994 | Judet |
| 5,326,359 A | 7/1994 | Oudard |
| 5,358,526 A | 10/1994 | Tornier |
| 5,405,399 A | 4/1995 | Tornier |
| 5,429,639 A | 7/1995 | Judet |
| 5,458,650 A | 10/1995 | Carret et al. |
| 5,505,731 A | 4/1996 | Tornier |
| 5,591,168 A | 1/1997 | Judet et al. |
| 5,662,651 A | 9/1997 | Tornier et al. |
| 5,676,702 A | 10/1997 | Ratron |
| 5,702,447 A | 12/1997 | Walch et al. |
| 5,702,457 A | 12/1997 | Walch et al. |
| 5,702,478 A | 12/1997 | Tornier |
| 5,766,256 A | 6/1998 | Oudard et al. |
| 5,824,106 A | 10/1998 | Fournol |
| 5,871,018 A | 2/1999 | Delp et al. |

(Continued)

FOREIGN PATENT DOCUMENTS
DE 10309500 9/2004
(Continued)

OTHER PUBLICATIONS

Rochetin, U.S. Appl. No. 11/194,452, entitled "Patellar Retractor and Method of Surgical Procedure on Knee," filed Aug. 2, 2005.

(Continued)

*Primary Examiner* — Bruce E Snow
*Assistant Examiner* — Melissa Hoban
(74) *Attorney, Agent, or Firm* — Faegre & Benson LLP

(57) ABSTRACT

This surgical apparatus comprises, on the one hand, means for spatial marking-out of the patella and femur of a patient to be operated on, and, on the other hand, means for simultaneous and relative representation of this patella provided virtually with a patellar implant of the prosthesis, and of this femur provided virtually with a femoral implant of the prosthesis, in a transverse plane passing both through the patella and through the trochlea of the aforementioned femoral implant. Using this apparatus, the surgeon can easily and quickly check the congruent position of the patellar implant with respect to the prosthetic femoral trochlea in order to reduce the risks of subsequent dislocations of the patella fitted with the prosthesis.

27 Claims, 3 Drawing Sheets

U.S. PATENT DOCUMENTS

| | | | |
|---|---|---|---|
| 5,879,395 | A | 3/1999 | Tornier et al. |
| 6,002,859 | A | 12/1999 | DiGioia, III et al. |
| 6,162,254 | A | 12/2000 | Timoteo |
| 6,165,224 | A | 12/2000 | Tornier |
| 6,168,629 | B1 | 1/2001 | Timoteo |
| 6,171,341 | B1 | 1/2001 | Boileau et al. |
| 6,183,519 | B1 | 2/2001 | Bonnin et al. |
| 6,205,411 | B1 | 3/2001 | DiGioia, III et al. |
| 6,206,925 | B1 | 3/2001 | Tornier |
| 6,299,646 | B1 | 10/2001 | Chambat et al. |
| 6,328,758 | B1 | 12/2001 | Tornier et al. |
| 6,334,874 | B1 | 1/2002 | Tornier et al. |
| 6,379,387 | B1 | 4/2002 | Tornier |
| 6,454,809 | B1 | 9/2002 | Tornier |
| 6,488,712 | B1 | 12/2002 | Tornier et al. |
| 6,540,770 | B1 | 4/2003 | Tornier et al. |
| 6,582,469 | B1 | 6/2003 | Tornier |
| 6,599,295 | B1 | 7/2003 | Tornier et al. |
| 6,626,946 | B1 | 9/2003 | Walch et al. |
| 6,761,740 | B2 | 7/2004 | Tornier |
| 6,767,368 | B2 | 7/2004 | Tornier |
| 6,802,864 | B2 | 10/2004 | Tornier |
| 6,824,567 | B2 | 11/2004 | Tornier et al. |
| 6,890,357 | B2 | 5/2005 | Tornier |
| 6,969,406 | B2 | 11/2005 | Tornier |
| 7,033,396 | B2 | 4/2006 | Tornier |
| 7,468,077 | B2 | 12/2008 | Rochetin |
| 7,547,307 | B2 | 6/2009 | Carson et al. |
| 7,611,519 | B2 | 11/2009 | Lefevre et al. |
| 2003/0009170 | A1 | 1/2003 | Tornier |
| 2003/0009171 | A1 | 1/2003 | Tornier |
| 2003/0028198 | A1 | 2/2003 | Tornier et al. |
| 2003/0212403 | A1 | 11/2003 | Swanson |
| 2004/0044295 | A1* | 3/2004 | Reinert et al. ............... 600/587 |
| 2004/0134821 | A1 | 7/2004 | Tornier |
| 2004/0169673 | A1 | 9/2004 | Crampe et al. |
| 2004/0210220 | A1 | 10/2004 | Tornier |
| 2004/0215200 | A1 | 10/2004 | Tornier et al. |
| 2004/0230197 | A1 | 11/2004 | Tornier et al. |
| 2005/0021044 | A1 | 1/2005 | Stone et al. |
| 2005/0049709 | A1 | 3/2005 | Tornier |
| 2005/0055102 | A1 | 3/2005 | Tornier et al. |
| 2005/0101966 | A1 | 5/2005 | Lavallee |
| 2005/0165490 | A1 | 7/2005 | Tornier |
| 2005/0203536 | A1 | 9/2005 | Laffargue et al. |
| 2005/0251026 | A1 | 11/2005 | Stone |
| 2005/0278030 | A1 | 12/2005 | Tornier et al. |
| 2005/0278031 | A1 | 12/2005 | Tornier et al. |
| 2005/0278032 | A1 | 12/2005 | Tornier et al. |
| 2005/0278033 | A1 | 12/2005 | Tornier et al. |
| 2005/0288791 | A1 | 12/2005 | Tornier et al. |
| 2006/0015185 | A1 | 1/2006 | Chambat et al. |
| 2006/0173457 | A1 | 8/2006 | Tornier |
| 2006/0235538 | A1 | 10/2006 | Rochetin et al. |
| 2006/0293613 | A1* | 12/2006 | Fatehi et al. ................. 600/587 |
| 2007/0032960 | A1 | 2/2007 | Altmann et al. |
| 2007/0078678 | A1 | 4/2007 | DiSilvestro et al. |
| 2007/0100258 | A1* | 5/2007 | Shoham et al. ............... 600/587 |
| 2007/0162142 | A1 | 7/2007 | Stone |
| 2007/0179626 | A1* | 8/2007 | de la Barrera et al. ..... 623/20.14 |
| 2007/0185498 | A2* | 8/2007 | Lavallee ....................... 606/102 |
| 2007/0270718 | A1 | 11/2007 | Rochetin |
| 2008/0154127 | A1 | 6/2008 | DiSilvestro et al. |
| 2008/0208081 | A1 | 8/2008 | Murphy et al. |
| 2008/0255445 | A1 | 10/2008 | Neubauer et al. |
| 2008/0262812 | A1 | 10/2008 | Arata et al. |
| 2008/0287781 | A1 | 11/2008 | Revie et al. |
| 2008/0288228 | A1 | 11/2008 | Kouchi et al. |

FOREIGN PATENT DOCUMENTS

| | | | |
|---|---|---|---|
| WO | | 02/36031 | 5/2002 |
| WO | | 02/36031 A1 | 5/2002 |
| WO | WO | 0236031 A1 * | 5/2002 |
| WO | | 04/001569 | 12/2003 |
| WO | | 2004/019792 | 3/2004 |

OTHER PUBLICATIONS

Ratron et al., U.S. Appl. No. 11/626,735, entitled "Surgical Instrumentation Kit for Inserting an Ankle Prothesis," filed Jan. 24, 2007.

Rochetin, U.S. Appl. No. 11/670,274, entitled "Offset Stem Tibial Implantation," filed Feb. 1, 2007.

USPTO file wrapper for U.S. Appl. No. 11/401,414, "Surgical Apparatus for Implantation of a Partial or Total Knee Prosthesis," filed Apr. 11, 2006.

* cited by examiner

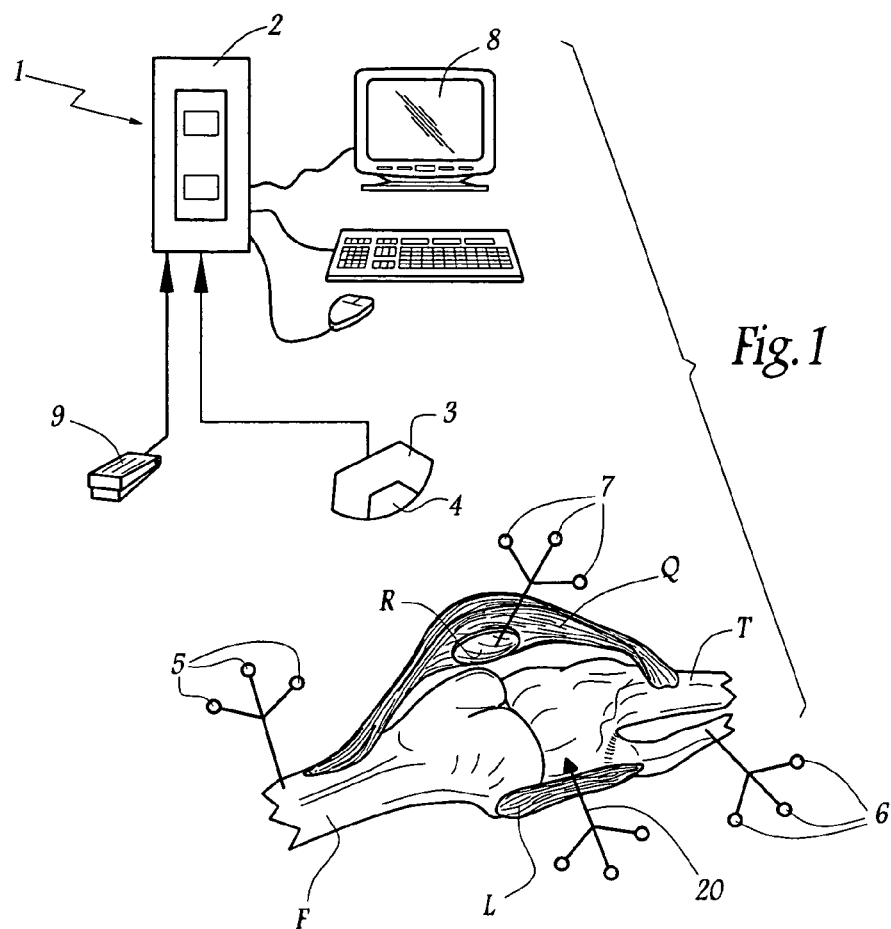
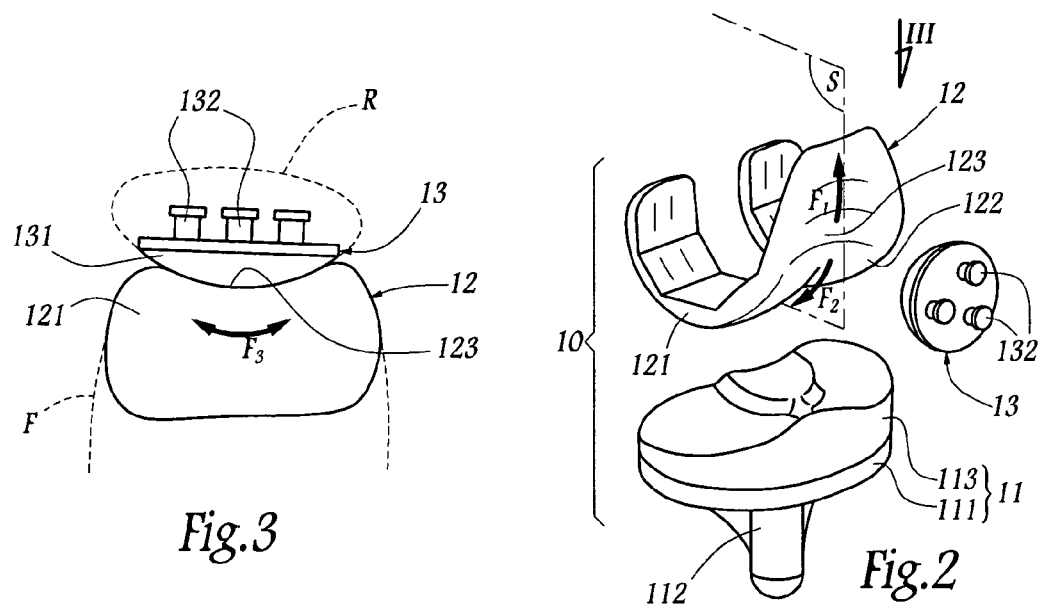

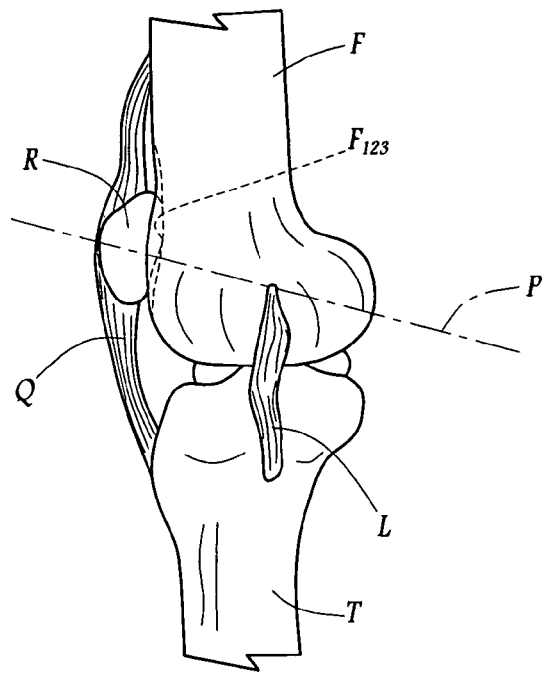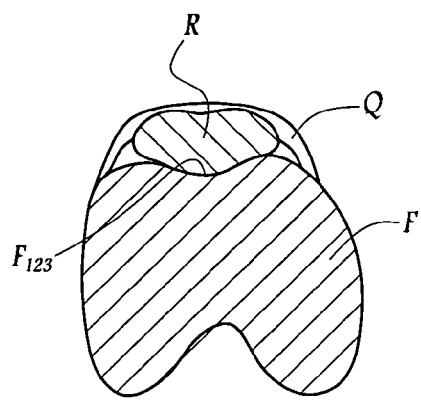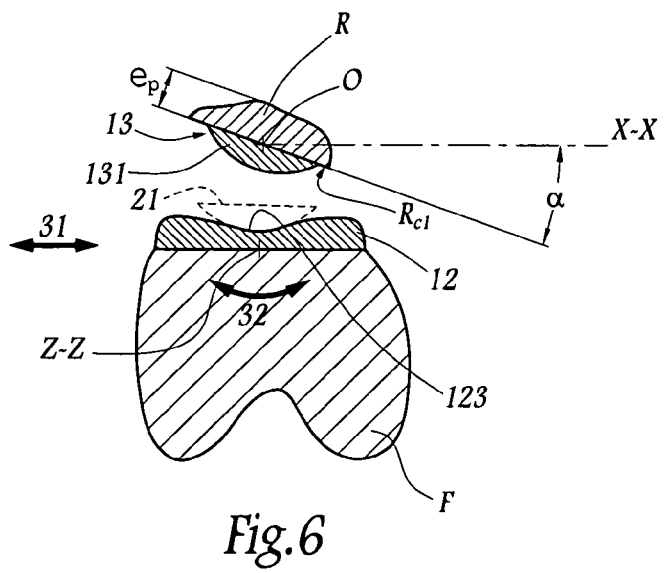
Fig.4
Fig.5
Fig.6

SURGICAL APPARATUS FOR IMPLANTATION OF A PARTIAL OR TOTAL KNEE PROSTHESIS

The present invention relates to a surgical apparatus for implantation of a partial or total knee prosthesis.

A total knee prosthesis conventionally comprises:
- a tibial part generally composed of a metal platform to be firmly connected to the resected upper end of the tibia, and of a polyethylene runner which rests, in a fixed or movable manner, on the upper face of the platform,
- a femoral component in the form of a generally metal hood which, on one side, is firmly connected to the resected lower end of the femur and which, on the other side, delimits two convex surfaces that approximately reproduce the geometry of two internal and external anatomical femoral condyles and are designed to rest in an articulated manner on two corresponding concave surfaces formed by the tibial runner, and
- a patellar implant firmly connected to the anatomical patella, on its posterior face, that is to say on its face directed towards the femur, after resurfacing of said face.

The success of the implantation of such a prosthesis and its subsequent mechanical hold during its working life are very much dependent on the relative positioning of the implanted prosthetic elements. In practice, it is found that the dislocations of the patella fitted with the prosthesis are among the most common causes of failure. The patellar implants are in fact conventionally fitted in place without any great consideration being paid to the femoral and tibial elements of the prosthesis, the surgeon generally being content to centre the patellar implant roughly on the resected posterior face of the anatomical patella. It is true that this bone is awkward to manoeuvre since it is held by the tendon of the quadriceps and the latter has to be turned aside in order to permit resurfacing of the then dislocated patella.

US-A-2003/0212403 proposes a method of fitting a total knee prosthesis intended to limit the invasive nature of the surgery. To this end, this document proposes spatially marking out simultaneously the bones of the tibia, femur and patella and using these markers to guide the surgeon's manoeuvres, without his having to completely incise the knee joint of the patient. The trauma suffered by the patient is thus reduced and the work of the surgeon is made easier. However, the positioning of the patellar implant is decided a priori by the surgeon solely on the basis of the anatomical information relating to the patella on which the prosthesis is to be fitted, without taking into consideration the implantation positions of the tibial and femoral prosthetic components. The risks of dislocation of the patella thus fitted with the prosthesis are therefore similar to those of a prosthesis implanted by a more invasive conventional method.

WO-A-02/36031 proposes a system for determinating the position of a knee prosthesis to be implanted, this system being able both to specially mark out the bones of the knee and to simultaneously display the patella to be fitted with the prosthesis and the lower end of the femur after that this end is fitted with the femoral prosthesis. This reference does not provide with any possibility of virtual representation of implants, contrary to reference WO-A-2004/001569 which, however, does not concern an improvement of the fitting of a pattelar implant. In these two references, the proposed representations are only in elevations of the bones, especially either in an elevation corresponding to the internal face of the patella or in an axial or frontal elevation of the intercondylar area of the femur in WO-A-02/36031. Such representations do not provide a sufficient precision to efficiently position the implants of a knee prosthesis, especially to limit the risks of dislocation of the patella thus fitted with the prosthesis.

The object of the present invention is to make available a surgical apparatus which affords simple, rapid and low-cost assistance to the surgeon during implantation of a partial or total knee prosthesis with a view to limiting the risk of subsequent dislocation of the patellar implant, by means of better adaptation to the other components of the implanted prosthesis, in particular the femoral implant.

To this end, the invention relates to a surgical apparatus for implantation of a partial or total knee prosthesis comprising at least a patellar implant and a femoral implant, said apparatus having:
- means for peroperative spatial marking-out of the bones of the patella and femur to be fitted with the prosthesis,
- means for peroperative representation that are designed to show, in a transverse plane passing both through the patella and through an intercondylar trochlea of the femoral implant, a simultaneous and relative representation of the patella which is to be fitted with the prosthesis and is provided virtually with the patellar implant, and of the lower part of the femur which is to be fitted with the prosthesis and is provided virtually with the femoral implant.

Using the apparatus according to the invention, the surgeon, during the surgical intervention, is able to view the representation of the patellar implant implanted virtually on the patella of a patient relative to the representation of the femoral implant implanted virtually on the femur of the patient and can thus check the congruence between the patellar implant to be implanted and the intercondylar trochlea of the femoral implant to be implanted. This is because the surgeon seeks to obtain the best possible congruence for the purpose of limiting the risk of any subsequent luxation of the patella with respect to the femoral implant, both on the internal side and the external side of the trochlea. This check is particularly effective in the transverse plane, that is to say substantially perpendicular to the tendon of the quadriceps and to the lateral tendons of the knee joint, which passes both through the bone of the patella and through the intercondylar trochlea of the femoral implant, since the external and internal transition zones between the trochlea and the prosthetic condyles are then clearly visible. In other words, the fact that this transverse plane passes through the bone tissue constituting the patella and the intercondylar trochlea provides a notable precision for the representation of the bones and of their virtual implants, which enables to quickly and efficiently figure the centering of the patellar implant with respect to the intercondylar trochlea, and the appropriate controls in order to implant this patellar implant on the patella. In the event that the representation means of the surgical apparatus according to the invention indicate to the surgeon that the expected congruence is insufficient, the surgeon can decide on surgical manoeuvres aimed at improving the implantation configuration, especially by modifying the geometry of implantation of the patellar implant and, if appropriate, that of the femoral implant.

According to other characteristics of this apparatus, taken either singly or in any of the technically possible combinations:
- the transverse plane in which the patella and the femur are represented by the representation means corresponds to a substantially median plane of the patella;
- it includes a memory containing data relating to a preferential predetermined positioning of the patellar implant relative to the femoral implant for all the anatomically allowable configurations of flexion-extension of the knee, and wherein the representation means are designed to represent, in the transverse plane and in a simultaneous and relative manner, both the patella fitted virtually with the prosthesis, the femur fitted virtually with the prosthesis, and an image for assisting the surgeon, represented over at least one part of the patellar implant, this assistance image being positioned with respect to the virtual femoral implant, depending on the knee's flexion-extension configuration considered, as a function of the data on preferential positioning that are contained in the memory;

the representation means are designed to represent the patella fitted virtually with the prosthesis, the femur fitted virtually with the prosthesis and, if appropriate, the image for helping the surgeon obtain different configurations of flexion-extension of the knee, the transverse plane in which these elements are represented by these means being fixed relative to the patella;

the representation means are designed to represent said elements over a continuous course of flexion-extension of the knee, in particular over the course of maximum flexion-extension that is anatomically allowable;

it comprises means of adjustment of the virtual implantation of the patellar implant on the patella;

in the case where the patellar implant is to be fitted level with a posterior cutting of the patella, the adjustment means are designed to modify the distance between a predetermined point of the anterior face of the patella and the patellar sectioning line in the transverse plane, the angle value of the patellar sectioning line relative to a predetermined direction, and/or the position of the patellar implant along the patellar sectioning line;

in the case where a set of several patellar implants of different respective sizes is provided, the adjustment means are designed to change the size of the implant shown;

it comprises:
  means for selecting and memorizing at least one configuration of implantation of the patellar implant set by the adjustment means,
  an ancillary used for resurfacing the anterior face of the patella and equipped with spatial marking means, and
  means for comparing the resurfacing action effected by this ancillary with the data from the selecting and memorizing means;

it additionally comprises other means for simultaneous and relative representation of the patella which is to be fitted with the prosthesis and is provided virtually with the patellar implant, and of the lower part of the femur which is to be fitted with the prosthesis and is provided virtually with the femoral implant, in a sagittal plane passing both through the patella and the trochlea of the femoral implant.

The invention also relates to a surgical method for implantation of a partial or total knee prosthesis comprising at least a patellar implant and a femoral implant, in which method the following steps are carried out in succession in the peroperative period:

the bones of the patella and femur of a patient to be treated are spatially marked out, the patella which is to be fitted with the patellar implant and is provided virtually with the patellar implant and the lower part of the femur which is to be fitted with the prosthesis and is provided virtually with the femoral implant are represented in a simultaneous and relative representation, this representation being effected in a transverse plane passing both through the patella and also through an intercondylar trochlea of the femoral implant, the virtual implantation of the patellar implant on the patella and, if appropriate, the virtual implantation of the femoral implant on the femur is adjusted such that the posterior part of the patellar implant is received congruently in the femoral intercondylar trochlea, the configuration of implantation of the patellar implant obtained according to the adjustment is selected and memorized, and the real patellar implant is implanted on the patella of the patient according to the configuration of implantation that has been selected and memorized.

According to an advantageous characteristic of this method:

in relation to the position of the femoral implant virtually implanted on the spatially marked-out femur, the position of the patellar implant virtually implanted on the spatially marked-out patella is compared with a predetermined position of this patellar implant in which position the patellar and femoral implants are positioned in a congruent manner, and the virtual implantation of the patellar implant on the patella is adjusted in such a way that its position coincides substantially with the predetermined position.

The invention will be better understood from reading the following description which is given solely by way of example and in which reference is made to the attached drawings, in which:

FIG. 1 is a schematic view of part of a surgical apparatus according to the invention, applied to the knee of a patient to be operated on;

FIG. 2 is a perspective view of a total knee prosthesis to be implanted by means of the apparatus from FIG. 1;

FIG. 3 is a view, according to the arrow III indicated in FIG. 2, of part of the knee prosthesis in a possible state of functioning;

FIG. 4 is a schematic side view of the patient's knee joint;

FIG. 5 is a section along a plane P in FIG. 4;

FIG. 6 is a view illustrating the representation provided by the apparatus from FIG. 1, in the plane P;

Figure 7:
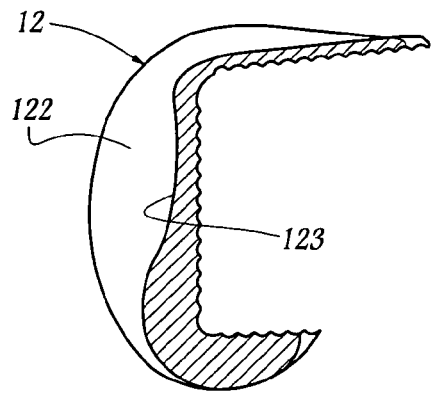
FIG. 7 is a sagittal cross section, along a plane S in FIG. 2, of the femoral component of the prosthesis from FIG. 2.

The surgical apparatus 1 in FIG. 1 comprises a computer 2 connected to a unit for transmission and reception of infrared radiation. This unit comprises a sensor 3 connected to the computer, and an infrared source 4 covering the operating field in which a part of a patient's knee that is to be treated is shown. The knee comprises the lower part of a femur F, the upper part of a tibia T, the tendon of the quadriceps Q which carries the bone of the patella R, and the lateral tendons L which connect the femur and the tibia.

The allow the computer 2 to spatially mark out the bones of the femur F, tibia T and patella R, the apparatus 1 comprises respective groups of markers 5, 6 and 7 which return, passively, the infrared radiation in the direction of the sensor 3. Each group of markers 5, 6 or 7 forms a three-dimensional marking system allowing the assembly made up of computer 2 and sensor 3 to spatially track the respective displacements of the femur, tibia and patella. The use of such markers is well known in the field of orthopaedics, for example in document EP-A-1 249 213, and they will not be described in any more detail below.

Each group of markers 5, 6 or 7 is fixed to the bone of the femur, the tibia or the patella by means of one or more rigid pins. These pins are positioned on the bones in such a way as to leave their markers permanently visible to the sensor 3.

The computer 2 of the apparatus 1 is also connected to one or more screens 8 for displaying information useful to the surgeon, in particular information relating to the relative position of the bones F, T and R, and other data described further below, preferably in the form of graphic representations, as detailed hereinafter.

The apparatus 1 also comprises control means 9, for example in the form of a pedal that can be activated by the surgeon's foot.

The surgical apparatus 1 additionally comprises other components which will be detailed hereinafter in the description of a detailed example of the use of this apparatus for implantation of a total knee prosthesis 10 represented alone in FIGS. 2 and 3. This prosthesis is made up of a tibial part 11 to be implanted in the bone of the tibia T, a femoral component 12 to be implanted in the bone of the femur F, and a patellar component 13 to be implanted on the bone of the patella R.

The tibial part 11 of the prosthesis 10 comprises a rigid and generally flat platform 111 provided, on one side, with a stub 112 for anchoring it in a previously resected upper end of the tibia T and equipped, on the opposite side, with a plateau or roller 113 which is connected to the platform in a fixed or movable manner depending on the type of prosthesis 10. On its face intended to be directed towards the femoral component 12, the plateau 113 defines two concave surfaces $113_1$ and $113_2$ which are designed to receive in an articulated manner two condyles, namely the internal condyle 121 and external condyle 122, which are formed by the femoral implant 12 and reproduce approximately the geometry of two anatomical femoral condyles. The condyles 121 and 122 delimit between them a femoral trochlea 123 which is intended to receive the patellar implant 13, as is shown in FIG. 3. For this purpose, the patellar implant comprises a button 131 having the overall shape of a spherical cap, and three stubs 132 which are used for anchoring in the posterior part of the patella and project forwards from the substantially plane anterior face of the button 131, whose centre is indicated by O. The concave curvature of the femoral trochlea 132 and the convex curvature of the patellar button 131 are dimensioned in such a way that the patellar implant 13 bears congruently on the femoral implant 12. This congruent contact thus permits, between the implants 12 and 13, a relative movement of translation along the femoral trochlea 123, as is shown by the arrows $F_1$ and $F_2$ in FIG. 2, and also movements of relative pivoting about the condyles 121 and 122, as is indicated by the double arrow $F_3$ in FIG. 3.

The prosthesis 10 described above is given only by way of example, and other prostheses of a different geometry and/or of a different nature can be implanted by means of the apparatus 1 according to the surgical implantation method described below. In particular, the invention applies to the implantation of partial knee prostheses, in particular to femoro-patellar prostheses composed of a patellar implant and of a femoral implant designed to bear directly on the upper end of the anatomical tibia and currently called a "trochlear implant".

In a first step, the surgeon makes an incision in the patient and collects a certain quantity of data relating to the anatomical geometry of the femur F, tibia T and patella R of the patient. For this purpose, different data acquisition means can be employed. By way of example, the surgeon uses a tracer 20 which is marked by the assembly of computer 2 and sensor 3 and which is previously calibrated. This tracer is moved to noteworthy sites of the bones to be marked out and, at each of these locations, the surgeon activates the control pedal 9 in such a way that the computer 2 records the position of the tracer and, in this way, deduces the anatomical characteristics of the femur F, tibia T and patella R. Based on these data, the tracking of the markers 5, 6 and 7 and pre-recorded data relating to a base geometry of the knee, the computer 2 is able to spatially mark out the bones F, T and R and monitor their relative displacements.

During this step of data acquisition, the tendon of the quadriceps Q is turned aside, as is shown in FIG. 1, in such a way that the reflecting markers 7 are visible to the sensor 3.

In a second step, the surgeon indicates to the computer 2 the model of the prosthesis 10 that he intends to implant. The choice of this prosthesis is either left to the entire discretion of the surgeon or is suggested by the computer, taking into consideration the morphological features, in particular the bone features, of the patient being operated on. The remainder of the description is based on the hypothesis that the surgeon selects the prosthesis 10 from FIGS. 2 and 3 as the one that he wishes to implant.

In a third step, the computer 2 supplies to the surgeon, via the screen 8, a virtual representation of the implantation configurations of the femoral component 12 and patellar component 13 of the prosthesis 10. More precisely, the computer displays on its screen 8 the patient's patella R which is provided virtually with the patellar implant 13, and the lower part of the femur F which is provided virtually with the femoral implant 12. To allow the surgeon to assess the congruency between the prosthetic button 131 and the prosthetic femoral trochlea 123, this representation is effected in a transverse plane P passing through both the patella R and also the prosthetic femoral trochlea 123.

To fully understand the benefit of this representation, FIG. 4 shows the anatomical knee joint from FIG. 1, it being understood that the joint shown does not display any noticeable structural anomaly. The joint is shown in the configuration of extension, so that the patella R bears on the anterior face of the lower end of the femur F at the level of the anatomical femoral trochlea $F_{123}$. By graphically sectioning this joint along the plane P indicated in FIG. 4, one observes in FIG. 5 the anatomical congruence of the posterior face of the patella R in relation to the anatomical trochlea $F_{123}$. This plane P is transverse to the patella, that is to say it is substantially perpendicular to the tendon of the quadriceps Q and to the lateral tendons L of the knee joint, thus cutting through the patella at the area of its internal and external flanks. By means of this representation in the plane P of both the patella R provided virtually with the patellar implant 13 and also of the femur F provided virtually with the femoral implant 12, the surgeon is provided with graph information representing the more or less congruent implantation of the femoral and patellar components of the prosthesis 10. An example of this representation is given in FIG. 6.

In practice, the transverse plane P corresponds advantageously to a substantially median plane of the patella R, that is to say a transverse plane on either side of which the bone material constituting the bone of the patella R is distributed in an almost identical manner. In this case, the plane P corresponds substantially to a plane of symmetry of the patellar button 131.

Thus, during the third operating step, the surgeon checks whether the virtual implantations of the patellar component 13 and femoral component 12 place the patellar button 131 congruently in the prosthetic femoral trochlea 123. If, as in FIG. 6, this congruent configuration is not obtained, the surgeon concludes that the implantation of the patellar implant 13 on the patella R and/or the implantation of the femoral implant 12 on the femur F are unsatisfactory and he corrects them. For this purpose, the computer 2 is equipped with means for adjustment of these virtual implantations, these means being controlled for example by touching the screen 8. In particular, the surgeon is then able to adjust the position of the line $R_{c1}$ sectioning the patella in the plane P, in particular its distance $e_p$ from the summit of the patella, and its angle α with respect to a mediolateral direction X-X relative to the patient, and also the position of the implant 13 along the line of sectioning $R_{c1}$. The aforementioned adjustment means also make it possible to change the size of the patellar implant 13, assuming the surgeon has available a set of such implants of different sizes held in the computer 2.

As regards the femoral implant 12, the aforementioned adjustment means advantageously allow modification of the size of this implant, its mediolateral position relative to the bone of the femur F, as is indicated by the double arrow 31 in FIG. 6, and/or its angular position relative to the femur about an overall vertical direction Z-Z fixed in advance, as is indicated by the double arrow 32.

To facilitate the adjustment of the virtual implantations of the prosthetic components 12 and 13, the representation in FIG. 6 advantageously includes the outline, shown by broken lines 21, in the plane P, of the prosthetic patellar button 131 in a predetermined position relative to the femoral implant 12. This predetermined position, whose geometric characteristics are provided for example by the manufacturer of the prosthesis 10, is the position considered to be optimal with a view to guaranteeing the best possible congruent configuration between the patellar and femoral components of the prosthesis. The surgeon is aided by this outline, since he is then able to modify the configurations of virtual implantation of the implants 12 and 13 so as to cause the patellar button 131 and the aforementioned outline 21 to come into coincidence with each other on the graph.

The congruence between the virtually implanted components 12 and 13 is advantageously checked when the patient's knee joint is in extension, as in FIGS. 4 and 5, but also when this joint is in flexion. Thus, for every flexed configuration of the knee selected by the surgeon, either on the basis of a corresponding computer command or by real bending of the patient's leg, whose movements are followed by the markers 5, 6 and 7, the computer displays a representation analogous to that in FIG. 6, including, if appropriate, an outline for helping the surgeon analogous to the outline 21, and the data relating to the different outlines in the different configurations of flexion-extension of the knee are delivered to and stored in the computer 2. The successive representations obtained are effected in the fixed plane P in relation to the patella R, while the section views of the femur F and of its virtual implant 12 develop as a function of the flexion-extension of the knee, according to the relative displacements between the patella and the femur. The adjustment of the virtual implantation of the prosthetic components 12 and 13 is thus possible irrespective of the degree of flexion of the patient's leg. The congruence can therefore be checked over the course of flexion most critical from the point of view of the risks of subsequent dislocations of the patella, that is to say for the degrees of flexion between about 0 and 30°.

Alternatively, the checking of the congruency and the adjustment of the virtual implantation of the prosthetic components 12 and 13 are carried out only for a discrete series of configurations of flexion of the knee joint, these configurations being chosen by the surgeon as being the most critical from the point of view of the risks of dislocation of the patella.

At the end of this third operating step, the surgeon has the computer 2 memorize the configurations of virtual implantation in the plane P of the prosthetic components 12 and 13 that he has set.

In a fourth step, the surgeon checks that the antero-posterior size of the femoral component 12 and patellar component 13 of the prosthesis is substantially identical to the corresponding anatomical size presented by the patient, so that the prosthesis, once implanted, does not significantly disturb the muscle tension and ligament tension of the patient's joint. To this end, the computer 2 provides the surgeon with a simultaneous and relative representation of the patella R provided virtually with the patellar implant 13 and of the lower part of the femur F provided virtually with the femoral implant 12, specifically in a sagittal plane passing both through the patella and the prosthetic femoral trochlea 123, as shown in FIG. 9.

Figure 8:
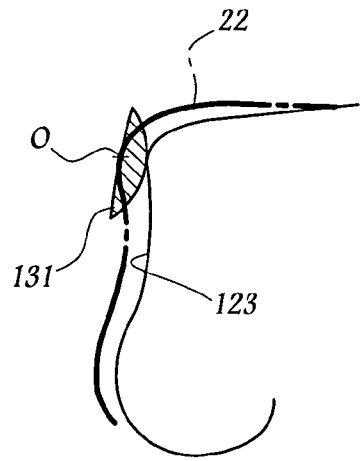
FIG. 8 is a diagram showing the trajectory of the patellar implant of the prosthesis from FIG. 2 relative to the femoral implant, during a flexion-extension movement of the knee prosthesis.

To fully understand the benefit of this representation in the aforementioned sagittal plane, the section of the femoral implant 12 in this plane is shown in FIG. 7. In practice, the sagittal plane in question corresponds to the plane S indicated in FIG. 2 passing through the base line of the trochlea 123. FIG. 8 shows, in the plane S, a line 22 which corresponds to the theoretical trajectory of the centre O of the patellar button 131 relative to the femoral implant 12 when this button is displaced in the prosthetic trochlea 123 during a movement of flexion-extension of the knee prosthesis 10. The data relating to the line 22 are, for example, supplied by the manufacturer of the prosthesis 10. This line is representative of an optimal implantation of the patellar component 13 from the point of view of the antero-posterior spacing between this component 13 and the femoral component 12. In other words, to guarantee that the antero-posterior part of the contact between the patella button 131 of the subsequently fitted implant 13 and the femoral trochlea 123 of the subsequently fitted implant 12 is as close as possible to that associated with the prosthesis 10, the implantations of the components 12 and 13 must as far as possible tend to place on the line 22 the centre O of the actually implanted patella button 131 in relation to the actually implanted femoral component 12.

Figure 9:
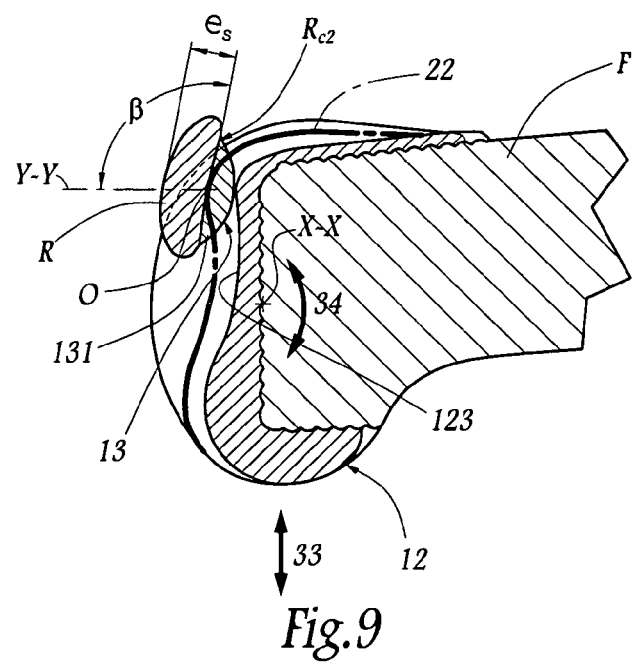
FIG. 9 is a view illustrating another representation provided by the apparatus from FIG. 1, in the plane S.

Thus, by virtue of the representation in FIG. 9, the surgeon is able to check, advantageously during a continuous stressing in flexion-extension of the leg, or for only some configurations of flexion of the knee joint chosen by the surgeon, that the centre of the virtual patella button 131 is situated on or in immediate proximity to the theoretical line 22 described above, of which the characteristic data have been delivered beforehand to the computer 2. This is for example the case in FIG. 9 where the knee joint is shown in approximately 60° flexion. The subsequent implantation of the components 12 and 13 will thus make it possible to obtain the expected prosthetic kinematics without significantly disturbing the surrounding muscles and ligaments of the knee that is being operated on.

In the event that the centre O is too far away from the line 22, the surgeon modifies the implantation configuration of the virtual patellar implant 13 and/or the implantation configuration of the virtual femoral implant 12. As regards the virtual patellar implantation, the surgeon, using adjustment means analogous to those described above in respect of FIG. 6 and held by the computer 2 and the screen 8, is able to modify the position of the section line $R_{c2}$ of the patella in the sagittal plane S, in particular its distance $e_s$ in relation to the summit of the anterior face of the patella and its angle β in relation to an antero-posterior direction Y-Y, and also the position of the implant 13 along the section line $R_{c2}$.

Alternatively, the outline of the line 22 is not supplied to the surgeon on the screen 8, so that the surgeon adjusts the implantation parameters on the basis of only the display of the virtual implants 12 and 13 relative to the bones of the femur F and patella R.

In the event that a set of several patellar implants 13 of different sizes is available and that the data relating to this set have been supplied beforehand to the computer 2, the aforementioned adjustment means also make it possible to change the size of the virtual implant 13 shown by the apparatus 1.

As regards the femoral implant 12, the adjustment means advantageously make it possible to modify the size of this implant if a set of several femoral implants is provided, its antero-posterior position relative to the femur F, as indicated by the double arrow 33 in FIG. 9, and/or its annular position relative to the femur about the mediolateral direction X-X as indicated by the double arrow 34.

At the end of this fourth operating step, the surgeon has the computer 2 memorize the configurations of virtual implantation, in the plane S, of the prosthetic components 12 and 13 that he has set.

In a fifth operating step, the surgeon resects the upper end of the tibia T, the lower end of the femur F and the posterior part of the patella R. To do so, the surgeon uses ancillary cutting devices marked out permanently by the computer 2, in such a way that the latter guides the surgeon's manoeuvres for resecting the aforementioned bones according to the implantation configurations that have previously been selected, in particular the patellar implantation configuration. The document US-A-2003/0212403 describes, for example, the use of tibial, femoral and patellar cutting guides that can be marked out by the computer 2.

It will be noted that the patellar sectioning plane is deduced by the computer 2 from the data relating to the sectioning lines $R_{c1}$ and $R_{c2}$ which were set during the third and fourth operating steps.

In a sixth operating step, the surgeon implants the components 11, 12 and 13 of the prosthesis 10 in the resected surfaces of the corresponding bones T, S and R.

The apparatus 1 according to the invention thus makes it possible to position the prosthesis 10 in an optimal manner for reducing as far as possible the risks of subsequent dislocations of the patellar component 13.

It will be noted that the six operating steps described above are carried out during an actual surgical intervention, that is to say during which, for example, the patient is under anaesthetic.

Moreover, the different data recorded during the fitting of the prosthesis can be used to draw up a post-operative record and to thus characterize with precision the articulation capacities of the prosthesis in its implantation state. It will be noted, however, that the amount of data acquired is much less than that necessary for the functioning of a biomechanical simulator of the knee, and that the corresponding computing means of the apparatus according to the invention are less costly and less complex to operate.

Various refinements and variations of the implantation apparatus 1 described above are also conceivable. By way of example, the means for marking out the bones F, T and R are not limited to the infrared reflection markers; for example, markers sensitive to ultrasound or to electromagnetic fields can be used.

The invention claimed is:

1. A surgical method for implantation at an intersection of a femur, tibia and patella in a knee joint of a patient a partial or total knee prosthesis that includes at least a patellar implant and a femoral implant, the method comprising per-operatively performing the steps of:
    recording in a computer data relating to an anatomical geometry of the knee joint proximate the intersection of the femur, the tibia and the patella;
    identifying in the computer the partial or total knee prosthesis;
    displaying on a computer screen a virtual implantation of the patellar implant in the patella and the femoral implant in the femur;
    assessing on the computer screen congruency between the patellar implant and a prosthetic femoral trochlea on the femoral implant displayed in a transverse plane passing through both the patella and the prosthetic femoral trochlea; and
    recording in the computer a virtual implantation in the transverse plane of the patellar implant and the femoral implant.

2. The method of claim 1 comprising the step of monitoring in the computer the relative displacement of the femur, tibia and patella.

3. The method of claim 1 wherein the step of identifying in the computer the partial or total knee prosthesis comprises manually entering a model of the partial or total knee prosthesis into the computer.

4. The method of claim 1 wherein the computer performs the steps of:
    evaluating the data relating to the anatomical geometry of one or more of the femur, tibia and patella of the patient; and
    suggesting a partial or total knee prosthesis based on morphological features of the patient.

5. The method of claim 1 wherein the transverse plane substantially comprises a plane of symmetry of the patella.

6. The method of claim 1 comprising the steps of adjusting the virtual implantation in the computer.

7. The method of claim 1 comprising selecting one or more of a different size patellar implant or femoral implant in response to adjustments of the virtual implantation in the computer.

8. The method of claim 1 comprising the steps of adjusting the congruency between the patellar implant and the prosthetic femoral trochlea by changing in the computer a sectioning angle of the patella relative to a mediolateral direction.

9. The method of claim 1 comprising the step of checking the congruency between the patellar implant and the prosthetic femoral trochlea with the knee joint in one of extension or flexion.

10. The method of claim 1 comprising the step of checking the congruency between the patellar implant and the prosthetic femoral trochlea by moving the knee joint through extension and flexion.

11. The method of claim 1 comprising the step of checking the congruency of the patellar implant to the prosthetic femoral trochlea by moving the knee joint through flexion between about zero degrees to about 30 degrees.

12. The method of claim 1 comprising implanting the patella implant and the femoral implant according to the virtual implantation recorded in the computer.

13. The method of claim 1 comprising the steps of:
    displaying on the computer screen the virtual implantation of the patellar implant in the patella and the femoral implant in the femur in a sagittal plane passing through both the patella and the prosthetic femoral trochlea; and
    evaluating on the computer screen the antero-posterior size of the femoral implant and the patellar implant.

14. The method of claim 1 comprising the step of displaying on the computer screen in a sagittal plane a theoretical trajectory of a center of the patellar implant relative to engagement with the femoral prosthetic trochlea during flexion-extension of the partial or total knee prosthesis.

15. The method of claim 14 wherein the theoretically trajectory comprises an optimal implantation of the patellar implant relative to the antero-posterior spacing between the femoral implant and the patellar implant.

16. The method of claim 1 comprising sizing the femoral implant and the patellar implant to generally match a theoretical trajectory of a center of the patellar implant relative to engagement with the femoral prosthetic trochlea as viewed in a sagittal plane.

17. The method of claim 1 comprising the step of modifying in the computer the virtual implantation of the patellar implant in the patella and the femoral implant in the femur in response antero-posterior spacing between the femoral implant and the patellar implant as viewed in a sagittal plane.

18. The method of claim 17 wherein the step of modifying comprises changing an angle of a section line of the patella in the sagittal plane.

19. The method of claim 17 wherein the step of modifying comprises changing a distance between the center of the patellar implant and an anterior face of the patella.

20. The method of claim 17 wherein the step of modifying comprises modifying the annular position of the femoral implant relative to the femur about the mediolateral direction.

21. The method of claim 1 comprising recording in the computer a virtual implantation in a sagittal plane of the patellar implant and a femoral implant.

22. The method of claim 1 comprising the step of the computer directing resection of an upper end of the tibia, a lower end of the femur and a posterior part of the patella according to the virtual implantation.

23. The method of claim 22 comprising implanting the patellar implant, the femoral implant and a tibial implant on resected surface of the tibia, femur and patella.

24. A surgical method for implantation at an intersection of a femur, tibia and patella in a knee joint of a patient a partial or total knee prosthesis that includes at least a patellar implant and a femoral implant, the method comprising per-operatively performing the steps of:
    recording in a computer data relating to an anatomical geometry of the knee joint proximate the intersection of the femur, the tibia and the patella;
    identifying in the computer the partial or total knee prosthesis;
    displaying on a computer screen a virtual implantation of the patellar implant in the patella and the femoral implant in the femur;
    assessing on the computer screen congruency between the patellar implant and a prosthetic femoral trochlea on the femoral implant displayed in a transverse plane passing through both the patella and the prosthetic femoral trochlea;
    adjusting in the computer the congruency between the patellar implant and the prosthetic femoral trochlea;
    selecting one or more of a different size patellar implant or femoral implant in response to adjustments of the virtual implantation in the computer; and
    recording in the computer the virtual implantation of the patellar implant and the femoral implant.

25. The method of claim 24 comprising the step of checking the congruency between the patellar implant and the prosthetic femoral trochlea with the knee joint in one of extension or flexion.

26. The method of claim 24 comprising the step of checking the congruency between the patellar implant and the prosthetic femoral trochlea by moving the knee joint through extension and flexion.

27. A surgical method for implantation at an intersection of a femur, tibia and patella in a knee joint of a patient a partial or total knee prosthesis that includes at least a patellar implant and a femoral implant, the method comprising per-operatively performing the steps of:
    recording in a computer data relating to an anatomical geometry of the knee joint proximate the intersection of the femur, the tibia and the patella;
    identifying in the computer the partial or total knee prosthesis;
    displaying on a computer screen a virtual implantation of the patellar implant in the patella and the femoral implant in the femur;
    assessing on the computer screen congruency between the patellar implant and a prosthetic femoral trochlea on the femoral implant displayed in a transverse plane passing through both the patella and the prosthetic femoral trochlea;
    evaluating on the computer screen the antero-posterior size of the femoral implant and the patellar implant displayed in a sagittal plane passing through both the patella and the prosthetic femoral trochlea; and
    recording in the computer the virtual implantation of the patellar implant and the femoral implant.

* * * * *